US007306856B2

(12) United States Patent
Igarashi et al.

(10) Patent No.: US 7,306,856 B2
(45) Date of Patent: Dec. 11, 2007

(54) LIGHT-EMITTING ELEMENT AND IRIDIUM COMPLEX

(75) Inventors: Tatsuya Igarashi, Kanagawa (JP); Toshihiro Ise, Kanagawa (JP); Yousuke Miyashita, Kanagawa (JP); Hidetoshi Fujimura, Kanagawa (JP); Hisashi Okada, Kanagawa (JP); Masayuki Mishima, Kanagawa (JP); Qiu Xuepeng, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 09/905,996

(22) Filed: Jul. 17, 2001

(65) Prior Publication Data

US 2002/0024293 A1 Feb. 28, 2002

(30) Foreign Application Priority Data

Jul. 17, 2000 (JP) .............................. 2000-216338

(51) Int. Cl.
*H01L 51/54* (2006.01)
(52) U.S. Cl. .................. 428/690; 428/917; 313/504; 313/506; 257/40; 257/E51.044
(58) Field of Classification Search ................ 313/483, 313/504, 506; 546/2, 4, 10; 428/690, 917; 257/40; 252/301.16
See application file for complete search history.

(56) References Cited

U.S. PATENT DOCUMENTS

| 5,391,681 | A | 2/1995 | Mühlebach et al. |
| 5,645,948 | A | 7/1997 | Shi et al. |
| 6,084,250 | A * | 7/2000 | Justel et al. ................. 257/89 |
| 6,184,618 | B1 * | 2/2001 | Justel et al. ................ 313/463 |
| 6,458,475 | B1 | 10/2002 | Adachi et al. |
| 6,670,645 | B2 * | 12/2003 | Grushin et al. .............. 257/98 |
| 2002/0028329 | A1 | 3/2002 | Ise et al. |
| 2002/0121638 | A1 * | 9/2002 | Grushin et al. .............. 257/40 |
| 2002/0182441 | A1 * | 12/2002 | Lamansky et al. ......... 428/690 |
| 2002/0197511 | A1 | 12/2002 | D'Andrade et al. |

FOREIGN PATENT DOCUMENTS

| EP | 0 387 715 A2 | 9/1990 |
| EP | 0 825 804 A2 | 2/1998 |
| WO | WO 99/20081 A2 | 4/1999 |
| WO | 00/57676 | 9/2000 |
| WO | 00/70655 | 11/2000 |
| WO | 01/41512 A1 | 6/2001 |

OTHER PUBLICATIONS

"Very high-efficiency green organic light-emitting devices based on electrophoresecence", Baldo et al., Applied Physics Letters, vol. 75, No. 1, Jul. 5, 1999, pp. 4-6.*

"Photochemistry and Luminescence of Cyclometallated Complexes", Maestri et al., Advances in Photochemistry, vol. 17, 1992, pp. 1-69.*

U.S. Appl. No. 60/283,814 (Apr. 2001).*

"Very high-efficiency green organic light-emitting devices based on electrophosphorescence", Applied Physics letters, vol. 75, No. 1, Jul. 5, 1999.

"Ir (III) cyclometalated complexes as efficient phosphorescent emitters in polymer blend and organic led's", Polymer Preprints 2000, 41 (1), 770.

Maria D S M et al., "Aromatic propellenes. Part 10. Conformational study of hexa (imidazol-1-yl) benzene and hexakis (2-methylimidazol-1-yl) benzene by means of NMR and AM1 calculations" *Journal of Molecular Structure*, vol. 478, 1999, pp. 285-294, XP002194812.

Cheng L F et al., "Photoemission study of a new electroluminescent material; trimer of N-arylbenzimidazoles (TPBI)" *Displays*, vol. 21, 2000, pp. 51-54 XP002194813.

Viktor Milata et al., "2,4,6-Tris(azol-1-yl)-1,3,5-Triazines: A New Class of Multidentate Ligands", Heterocycles 55(5), May 1, 2001, pp. 905-924.

(Continued)

*Primary Examiner*—Marie Yamnitzky
(74) *Attorney, Agent, or Firm*—Sughrue Mion, Pllc.

(57) ABSTRACT

A light-emitting element having excellent light-emitting properties and with which it is possible to emit blue light at a high luminance for a long period of time, and an iridium complex for realizing the same. The light-emitting element has an external quantum efficiency of at least 5% and a light emission maximum wavelength λmax of no more than 500 nm. Further, there is provided a light-emitting element including a light-emitting layer or a plurality of organic compound layers having the light-emitting layer, with at least one of the compound layers including at least one kind of a compound having a partial structure represented by the general formula K-0. In the general formula K-0, $R^1$ to $R^7$ each independently represents a hydrogen atom or a substituent, provided that if $R^2$ is a fluorine atom, $R^3$ is not a hydrogen atom

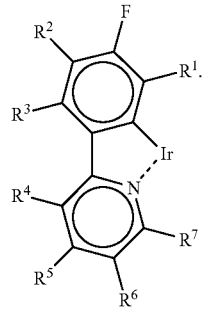

K-0

15 Claims, No Drawings

OTHER PUBLICATIONS

ZCAPLUS 1998:699652; abstract for Pilar Cornago et al., "Aromatic propellenes. Part 9. Synthesis and conformational study of hexakis (benzimidazol-1-yl)benzene", ACH-Models in Chemistry 135(4), 1998, pp. 475-483.

Chihaya Adachi et al., "Endothermic energy transfer: A mechanism for generating very efficient high-energy phosphorescent emission in organic materials", Applied Physics Letters 79(13), Sep. 24, 2001, pp. 2082-2084.

W. Kowalsky, et al., "Organic Light Emitting diodes", publication dated Apr. 21, 1996; XP 000634526; pp. 450-453.

* cited by examiner

LIGHT-EMITTING ELEMENT AND IRIDIUM COMPLEX

BACKGROUND OF THE INVENTION

1. Field of the Invention

The present invention relates to a novel iridium complex and a light-emitting element that uses the novel iridium complex. More particularly, the present invention relates to a novel iridium complex and a light-emitting element that uses the novel iridium complex that can be appropriately used in display elements, displays, backlights, electrophotography, illumination light sources, recording light sources, exposure light sources, read light sources, signs, signboards, interior optical communication and the like.

2. Description of the Related Art

At present, research and development relating to various kinds of display elements are actively being carried out. In particular, organic electroluminescent (EL) elements have received attention as promising display elements because EL elements can emit highly luminous light at a low voltage. For example, a light-emitting element having an organic thin film formed by vapor deposition of an organic compound has been known (*Applied Physics Letters,* Vol. 51, p. 913 (1987)). Light-emitting elements disclosed in the literature use tris(8-hydroxyquinolinate) aluminum complex (Alq) as an electron transporting material, and have a structure comprising a layer containing the electron transporting material and a layer containing a hole transporting material (an amine compound) laminated together. In comparison to conventional light-emitting elements comprising a single layer, light-emitting characteristics can be greatly improved with light-emitting elements comprising laminated layers. In recent years, the application of organic EL elements to color displays and white light sources has been actively investigated. In order to apply organic EL elements to such ends, it is necessary to improve the light-emitting properties of the organic EL elements, such as luminance and light-emitting lifespan, with regard to light-emitting elements that are capable of emitting light in blue, green and red colors, respectively.

As a light-emitting element having improved light-emitting properties, a light-emitting element utilizing light emission from an orthometalated iridium complex (Ir(ppy)$_3$: tris-orthometalated complex of iridium (III) with 2-phenylpyridine) has been reported (*Applied Physics Letters,* Vol. 75, p. 4 (1999)). While it has conventionally been said that the external quantum efficiency of light-emitting elements is limited to 5%, light-emitting elements disclosed in the literature reach an external quantum efficiency of 8%, which exceeds the conventional limitation. However, the emitted light obtained from the light-emitting element is limited to green light emission, and the applicable range as a display is narrow. The applicable range as a display could be expanded if light-emitting elements having improved light-emitting characteristics for other colors could be provided. Thus, there has been a demand to improve light-emitting characteristics of light-emitting elements of other colors.

With respect to blue light-emitting elements, various light-emitting elements have been reported that use a distyrylallylene derivative, represented by DPVBi (4,4'-bis(2,2'-diphenylvinyl)biphenyl), and an analog thereof. However, there have been no reports of blue light-emitting elements having an external quantum efficiency exceeding 5%. If a blue light-emitting element having an external quantum efficiency exceeding 5% could be provided, it would be possible for a highly efficient organic EL element to display multicolors and white color, whereby application of light-emitting elements would be greatly advanced. Moreover, it would be possible to greatly reduce electrical power consumption and to realize large area display and long term use when the light-emitting element is applied to a display element.

SUMMARY OF THE INVENTION

The present invention has been developed in view of the foregoing problems. An object of the invention is to provide a light-emitting element that can reduce energy consumption when light is emitted, that has excellent light-emitting properties, and with which it is possible to emit blue light at a high luminance for a long period of time.

Another object of the invention is to provide an iridium complex having excellent light-emitting properties and with which it is possible to emit blue light at a high luminance for a long period of time, and a light-emitting element that uses the iridium complex.

As means to accomplish these objects, the present invention provides the following light-emitting elements and iridium complexes:

(1) a light-emitting element having an external quantum efficiency of at least 5% and a light emission maximum wavelength λmax of no more than 500 nm;

(2) a light-emitting element containing a light-emitting material, with a phosphorescence quantum yield of the light-emitting material being at least 70% at 20° C. and a phosphorescence emission maximum wavelength λmax of the light-emitting material being no more than 500 nm;

(3) a light-emitting element comprising a light-emitting layer or a plurality of organic compound layers including the light-emitting layer disposed between a pair of electrodes, wherein at least one of the compound layers includes at least one kind of a compound having a partial structure represented by the following general formula K-0:

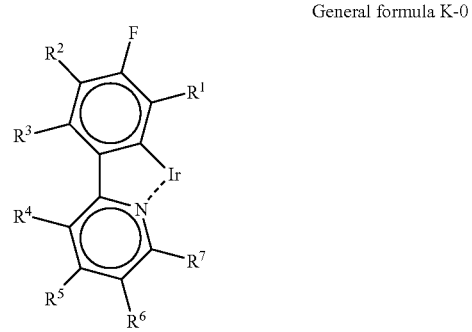

General formula K-0 wherein $R^1$ to $R^7$ each independently represents a hydrogen atom or a substituent, provided that if $R^2$ is a fluorine atom, $R^3$ is not a hydrogen atom;

(4) an iridium complex represented by the following general formula K-II:

General formula K-II

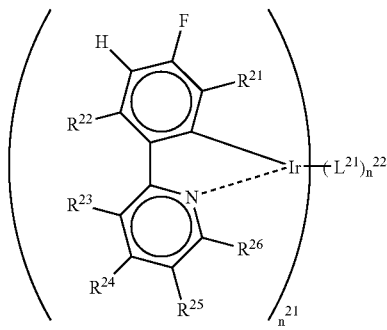

wherein $R^{21}$ to $R^{26}$ each independently represents a hydrogen atom or a substituent; $L^{21}$ represents a ligand; $n^{21}$ represents an integer of 1 to 3; and $n^{22}$ represents an integer of 0 to 4;

(5) an iridium complex represented by the following general formula K-IV:

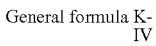
General formula K-IV

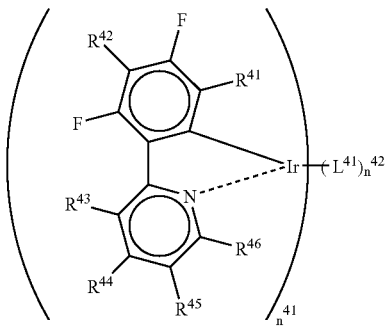

wherein $R^{41}$ to $R^{46}$ each independently represents a hydrogen atom or a substituent; $L^{41}$ represents a ligand; $n^{41}$ represents an integer of 1 to 3; and $n^{42}$ represents an integer of 0 to 4;

DETAILED DESCRIPTION OF THE PREFERRED EMBODIMENTS

The light-emitting element of the present invention is characterized in that it exhibits blue light emission at a light emission maximum wavelength λmax of 500 nm or less and a high light emission efficiency with an external quantum efficiency of 5% or more. Therefore, the light-emitting element of the present invention can reduce energy consumption at the time light is emitted and can emit highly luminous blue light for a long period of time. Particularly, when the light-emitting element of the present invention is used as a display element, it becomes possible to increase surface area. The external quantum efficiency referred to herein means the value calculated by the equation below. Examples of methods of calculating the external quantum efficiency of the light-emitting element include a method in which external quantum efficiency is calculated from luminance of emitted light, light emission spectrum, relative visibility curve and electric current density, and a method in which external quantum efficiency is calculated from electric current density and total number of emitted photons.

external quantum efficiency (%)=(total number of emitted photons/number of electrons injected in light-emitting element)×100

The external quantum efficiency of the light-emitting element is preferably 7% or more, and more preferably 10% or more. The light-emitting element of the present invention preferably has a light emission maximum wavelength λmax of from 390 to 495 nm, more preferably from 400 to 490 nm, and further preferably from 420 to 480 nm, from the standpoint of color purity of blue color.

The light-emitting element of the present invention may, as long as it has a light emission maximum wavelength of 500 nm or less, exhibit light emission in a wavelength region other than the blue region, such as an ultraviolet region, a green region and a red region.

It is preferable that an x value and a y value of the CIE chromaticity of light emission are as small as possible from the standpoint of the color purity of blue color. Specifically, the x value of the CIE chromaticity of light emission is preferably 0.22 or less, and more preferably 0.20 or less. The y value of the CIE chromaticity of light emission is preferably 0.53 or less, more preferably 0.50 or less, and further preferably 0.40 or less.

The light-emitting element preferably has a light emission spectrum half value width of 1 to 100 nm or less, more preferably from 5 to 90 nm, further preferably from 10 to 80 nm, and particularly preferably from 20 to 70 nm, from the standpoint of the color purity of blue color.

The light-emitting element is not particularly limited with respect to system, driving method and utility mode, and examples thereof include EL (electroluminescent) elements. One example of such an EL element includes a light-emitting element in which at least one light-emitting layer is formed between a pair of electrodes comprising an anode and a cathode. Other examples include a light-emitting element in which at least one of a hole implantation layer, a hole transporting layer, an electron implantation layer and an electron transporting layer is further disposed between the electrodes, in addition to the light-emitting layer. These layers may each have other functions, and various materials can be used to form each of the layers. The light-emitting element of the present invention is preferably an organic light-emitting element. The organic light-emitting element referred to herein means an element in which a material which exhibits emission of light is an organic compound.

In the light-emitting element, it is preferable that a layer containing a compound having an ionization potential of 5.9 eV or more, more preferably from 6.0 to 7.0 eV, is disposed between the cathode and the light-emitting layer, and it is more preferable that an electron transporting layer having an ionization potential of 5.9 eV or more is disposed between the cathode and the light-emitting layer.

In the light-emitting element, a material having a high phosphorescence quantum yield is preferably used as the light-emitting material. Specifically, a light-emitting material having a phosphorescence quantum yield of 70% or more at 20° C. and a phosphorescence emission maximum wavelength λmax of 500 nm or less is preferable. A light-emitting material having a phosphorescence quantum yield of 80% or more at 20° C. and a phosphorescence emission maximum wavelength λmax of 490 nm or less is more preferable. A light-emitting material having a phosphorescence quantum yield of 85% or more at 20° C. and a phosphorescence emission maximum wavelength λmax of 480 nm or less is still further preferable.

The above-described light-emitting material is a compound contained in a light emitting layer of the light emitting element, or in organic compound layers including the light emitting layer, which compound itself emits light. A transition metal complex is preferable as the light-emitting material, and an orthometalated complex is more preferable. Among orthometalated complexes, an iridium complex and a platinum complex are preferable, an orthometalated iridium complex is more preferable, and a compound having a partial structure represented by general formula K-0 (described later) is particularly preferable.

The orthometalated complex referred to herein is a generic designation of the group of compounds described in Akio Yamamoto, *Yûki Kinzoku Kagaku, Kiso to Ôyô* ("Organic Metal Chemistry, Fundamentals and Applications", Shôkabô, 1982), pp. 150 and 232, and in H. Yersin, *Photochemistry and Photophysics of Coordination Compounds* (New York: Springer-Verlag, 1987), pp. 71-77 and pp. 135-146.

The light-emitting element preferably contains, as the light-emitting material, the compound having the partial structure represented by the following general formula K-0 (hereinafter, sometimes referred to as "iridium compound"). Among iridium compounds, a compound having a phosphorescence quantum yield and a phosphorescence emission maximum wavelength λmax that are within the ranges described above is preferred. The general formula K-0 will be described in detail below.

The light-emitting material in the present invention functions in the state of being contained in the light-emitting layer of the light-emitting element or in a plurality of organic compound layers including the light-emitting layer.

General formula K-0

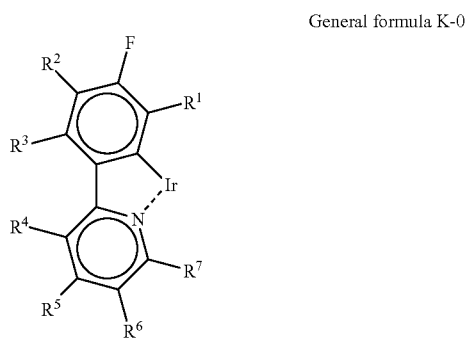

In the general formula K-0, $R^1$ to $R^7$ each independently represents a hydrogen atom or a substituent, provided that, if $R^2$ is a fluorine atom, $R^3$ shall not be a hydrogen atom. Examples of the substituent include groups, which will be described later for $R^{11}$ in the general formula K-0. $R^1$ in the general formula K-0 is preferably a hydrogen atom, an alkyl group, an aryl group or a heteroaryl group, and more preferably a hydrogen atom. $R^2$ in the general formula K-0 is preferably a hydrogen atom, an alkyl group, an aryl group, a heteroaryl group or a fluorine atom, and more preferably a hydrogen atom, fluorine atom, or alkyl group. $R^3$ in the general formula K-0 is preferably a hydrogen atom, an alkyl group, an aryl group, a heteroaryl group or a fluorine atom, more preferably a hydrogen atom or a fluorine atom, and further preferably a fluorine atom.

$R^5$ in the general formula K-0 is preferably a hydrogen atom, an alkyl group, a substituted or unsubstituted amino group or an alkoxy group, more preferably a hydrogen atom, alkyl group, or an alkoxy group, and further preferably a hydrogen atom. $R^4$, $R^6$, and $R^7$ are each preferably a hydrogen atom or an alkyl group, and more preferably a hydrogen atom.

In the general formula K-0, the valence of the iridium atom in the iridium compound is not particularly limited, and is preferably trivalent. The iridium compound may be a so-called single nucleus complex containing one iridium atom and may also be a so-called multinuclei complex containing two or more iridium atoms. Among these, a single nucleus complex containing one iridium atom is preferred. The iridium compound may contain a metallic atom other than iridium, and a compound containing a central metal being only an iridium atom is preferred.

The iridium compound may have various kinds of ligands in the structure thereof. Examples of the ligand include ligands disclosed in H. Yersin, *Photochemistry and Photophysics of Coordination Compounds* (New York: Springer-Verlag, 1987) and in Akio Yamamoto, *Yûki Kinzoku Kagaku, Kiso to Ôyô* ("Organic Metal Chemistry, Fundamentals and Applications", Shôkabô, 1982). The ligand may be either a unidentate ligand or a bidentate ligand. As the ligand, a halogen ligand (preferably a chlorine ligand), a nitrogen-containing heterocyclic ligand (such as phenylpyridine, benzoquinoline, quinolinole, bipyridyl and phenanthroline), a diketone ligand and a carboxylic acid ligand are preferred, and a diketone ligand (such as acetylacetone) is more preferred. The ligand contained in the iridium compound may be of one kind or two or more kinds. The ligand contained in the iridium compound is preferably of one or two kinds, and particularly of one kind. The iridium compound may be either a neutral complex having no electric charge or an anionic complex having a counter salt (such as a chloride ion, a $PF_6$ ion and a $ClO_4$ ion). Among these, a neutral complex is preferred.

The number of carbon atoms contained in the iridium compound is preferably from 15 to 100, more preferably from 20 to 70, and further preferably from 30 to 60.

The compound having the partial structure represented by the general formula K-0 is preferably a compound having a partial structure represented by the general formula K-I, or a compound having a partial structure represented by the general formula K-III, and more preferably a compound having a partial structure represented by the general formula K-III. The compound having the partial structure represented by the general formula K-I is preferably an iridium complex represented by the general formula K-II, and more preferably an iridium complex represented by the general formula K-V. The compound having the partial structure represented by the general formula K-III is preferably an iridium complex represented by the general formula K-IV, and more preferably an iridium complex represented by the general formula K-VI.

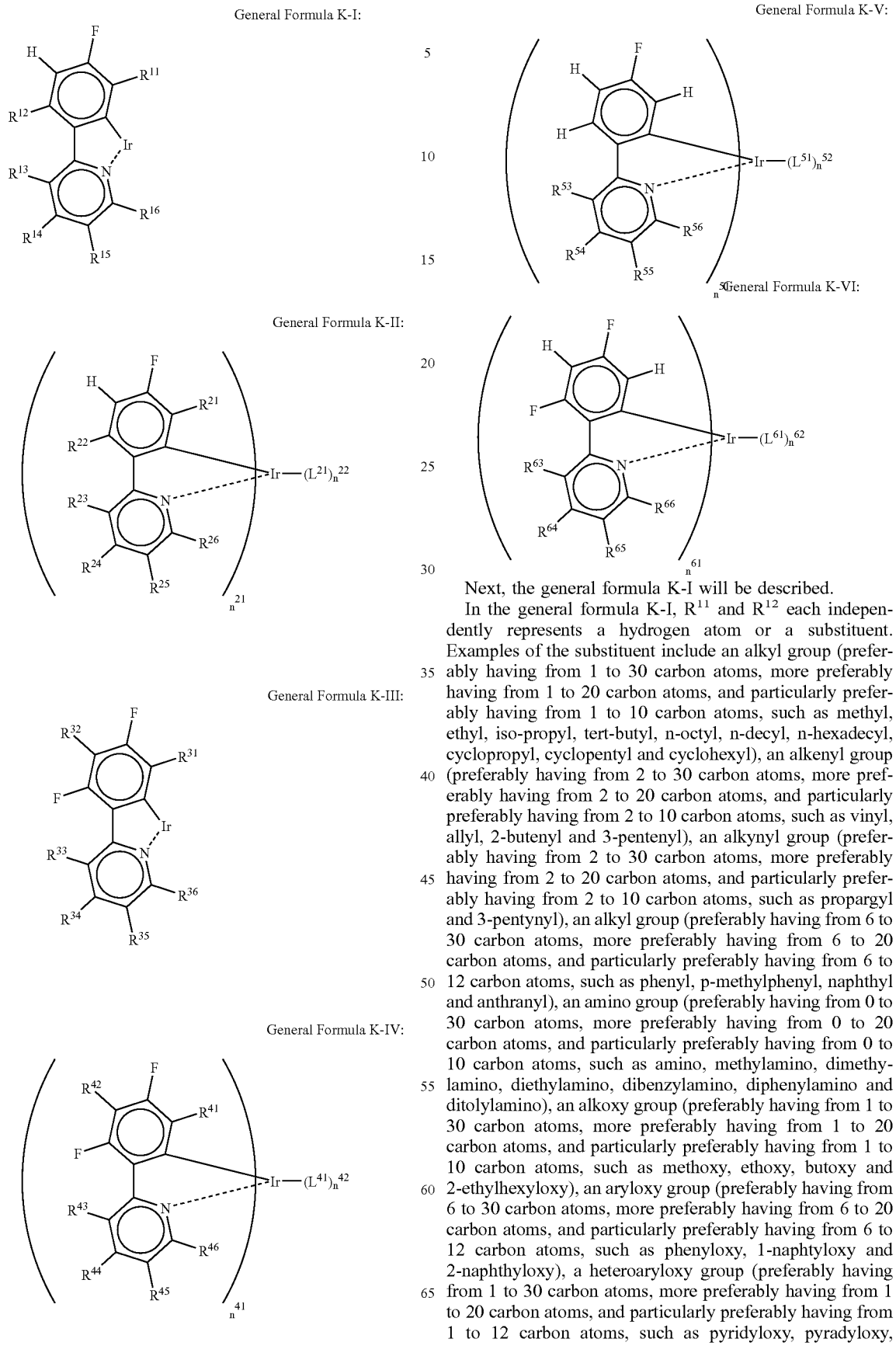

Next, the general formula K-I will be described.

In the general formula K-I, $R^{11}$ and $R^{12}$ each independently represents a hydrogen atom or a substituent. Examples of the substituent include an alkyl group (preferably having from 1 to 30 carbon atoms, more preferably having from 1 to 20 carbon atoms, and particularly preferably having from 1 to 10 carbon atoms, such as methyl, ethyl, iso-propyl, tert-butyl, n-octyl, n-decyl, n-hexadecyl, cyclopropyl, cyclopentyl and cyclohexyl), an alkenyl group (preferably having from 2 to 30 carbon atoms, more preferably having from 2 to 20 carbon atoms, and particularly preferably having from 2 to 10 carbon atoms, such as vinyl, allyl, 2-butenyl and 3-pentenyl), an alkynyl group (preferably having from 2 to 30 carbon atoms, more preferably having from 2 to 20 carbon atoms, and particularly preferably having from 2 to 10 carbon atoms, such as propargyl and 3-pentynyl), an alkyl group (preferably having from 6 to 30 carbon atoms, more preferably having from 6 to 20 carbon atoms, and particularly preferably having from 6 to 12 carbon atoms, such as phenyl, p-methylphenyl, naphthyl and anthranyl), an amino group (preferably having from 0 to 30 carbon atoms, more preferably having from 0 to 20 carbon atoms, and particularly preferably having from 0 to 10 carbon atoms, such as amino, methylamino, dimethylamino, diethylamino, dibenzylamino, diphenylamino and ditolylamino), an alkoxy group (preferably having from 1 to 30 carbon atoms, more preferably having from 1 to 20 carbon atoms, and particularly preferably having from 1 to 10 carbon atoms, such as methoxy, ethoxy, butoxy and 2-ethylhexyloxy), an aryloxy group (preferably having from 6 to 30 carbon atoms, more preferably having from 6 to 20 carbon atoms, and particularly preferably having from 6 to 12 carbon atoms, such as phenyloxy, 1-naphtyloxy and 2-naphthyloxy), a heteroaryloxy group (preferably having from 1 to 30 carbon atoms, more preferably having from 1 to 20 carbon atoms, and particularly preferably having from 1 to 12 carbon atoms, such as pyridyloxy, pyradyloxy, pyrimidyloxy and quinolyloxy), an acyl group (preferably having from 1 to 30 carbon atoms, more preferably having from 1 to 20 carbon atoms, and particularly preferably having from 1 to 12 carbon atoms, such as acetyl, benzoyl, formyl and pivaloyl), an alkoxycarbonyl group (preferably having from 2 to 30 carbon atoms, more preferably having from 2 to 20 carbon atoms, and particularly preferably having from 2 to 12 carbon atoms, such as methoxycarbonyl and ethoxycarbonyl), an aryloxycarbonyl group (preferably having from 7 to 30 carbon atoms, more preferably having from 7 to 20 carbon atoms, and particularly preferably having from 7 to 12 carbon atoms, such as phenyloxycarbonyl), an acyloxy group (preferably having from 2 to 30 carbon atoms, more preferably from 2 to 20 carbon atoms, and particularly preferably having from 2 to 10 carbon atoms, such as acetoxy and benzoyloxy), an acylamino group (preferably having from 2 to 30 carbon atoms, more preferably having from 2 to 20 carbon atoms, and particularly preferably having from 2 to 10 carbon atoms, such as acetylamino and benzoylamino), an alkoxycarbonylamino group (preferably having from 2 to 30 carbon atoms, more preferably having from 2 to 20 carbon atoms, and particularly preferably having from 2 to 12 carbon atoms, such as methoxycarbonylamino), an aryloxycarbonylamino group (preferably having from 7 to 30 carbon atoms, more preferably having from 7 to 20 carbon atoms, and particularly preferably having from 7 to 12 carbon atoms, such as phenyloxycarbonylamino), a sulfonylamino group (preferably having from 1 to 30 carbon atoms, more preferably having from 1 to 20 carbon atoms, and particularly preferably having from 1 to 12 carbon atoms, such as methanesulfonylamino and benzenesulfonylamino), a sulfamoyl group (preferably having from 0 to 30 carbon atoms, more preferably having from 0 to 20 carbon atoms, and particularly preferably having from 0 to 12 carbon atoms, such as sulfamoyl, methylsulfamoyl, dimethylsulfamoyl and phenylsulfamoyl), a carbamoyl group (preferably having from 1 to 30 carbon atoms, more preferably having from 1 to 20 carbon atoms, and particularly preferably having from 1 to 12 carbon atoms, such as carbamoyl, methylcarbamoyl, diethylcarbamoyl and phenylcarbamoyl), an alkylthio group (preferably having from 1 to 30 carbon atoms, more preferably having from 1 to 20 carbon atoms, and particularly preferably having from 1 to 12 carbon atoms, such as methylthio and ethylthio), an arylthio group (preferably having from 6 to 30 carbon atoms, more preferably having from 6 to 20 carbon atoms, and particularly preferably having from 6 to 12 carbon atoms, such as phenylthio), a heteroarylthio group (preferably having from 1 to 30 carbon atoms, more preferably having from 1 to 20 carbon atoms, and particularly preferably having from 1 to 12 carbon atoms, such as pyridylthio, 2-benzimidazolylthio, 2-benzoxazolylthio and 2-benzthiazolylthio), a sulfonyl group (preferably having from 1 to 30 carbon atoms, more preferably having from 1 to 20 carbon atoms, and particularly preferably having from 1 to 12 carbon atoms, such as mesyl and tosyl), a sulfinyl group (preferably having from 1 to 30 carbon atoms, more preferably having from 1 to 20 carbon atoms, and particularly preferably having from 1 to 12 carbon atoms, such as methanesulfinyl and benzenesulfinyl), an ureido group (preferably having from 1 to 30 carbon atoms, more preferably having from 1 to 20 carbon atoms, and particularly preferably having from 1 to 12 carbon atoms, such as ureido, methylureido and phenylureido), a phosphoamide group (preferably from 1 to 30 carbon atoms, more preferably from 1 to 20 carbon atoms, particularly preferably from 1 to 12 carbon atoms, such as diethylphos-phoamide and phenylphosphoamide), a hydroxyl group, a mercapto group, a halogen atom (such as a fluorine atom, a chlorine atom, a bromine atom and an iodine atom), a cyano group, a sulfo group, a carboxyl group, a nitro group, a hydroxamic acid group, a sulfino group, a hydrazino group, an imino group, a heterocyclic group (such as an aliphatic heterocyclic group and a heteroaryl group, preferably having from 1 to 30 carbon atoms, and more preferably having from 1 to 12 carbon atoms, examples of the hetero atom including a nitrogen atom, an oxygen atom and a sulfur atom, and examples of the heterocyclic group including imidazolyl, pyridyl, quinolyl, furyl, thienyl, piperidyl, morphorino, benzoxazolyl, benzimidazolyl, benzthiazolyl and carbazolyl), and a silyl group (preferably having from 3 to 40 carbon atoms, more preferably from 3 to 30 carbon atoms, and particularly preferably having from 3 to 24 carbon atoms, such as trimethylsilyl and triphenylsilyl). These substituents may further be substituted.

$R^{11}$ in the general formula K-I is preferably a hydrogen atom, an alkyl group, an aryl group or a heteroaryl group, and more preferably a hydrogen atom.

$R^{12}$ in the general formula K-I is preferably a hydrogen atom, an alkyl group, an aryl group, a heteroaryl group or a fluorine atom, more preferably a hydrogen atom or a fluorine atom, and further preferably a fluorine atom.

$R^{13}$, $R^{14}$, $R^{15}$, and $R^{16}$ in the general formula K-I each independently represents a hydrogen or a substituent. Two or more of substituents may be combined with each other to form a cyclic structure. The substituent may be any group of $R^{11}$. $R^{14}$ in the general formula K-I is preferably a hydrogen atom, an alkyl group, a substituted or unsubstituted amino group or an alkoxy group, more preferably a hydrogen atom, an alkyl group, or an alkoxy group, and particularly preferably a hydrogen atom.

$R^{13}$, $R^{15}$ and $R^{16}$ in the general formula K-I are each preferably a hydrogen atom or an alkyl group, and more preferably a hydrogen atom.

Next, the general formula K-II will be described. In the general formula K-II, $R^{21}$, $R^{22}$, $R^{23}$, $R^{24}$, $R^{25}$, and $R^{26}$ each has the same meaning as $R^{11}$, $R^{12}$, $R^{13}$, $R^{14}$, $R^{15}$, and $R^{16}$ in the general formula K-I, and preferred ranges thereof are also the same.

$L^{21}$ in the general formula K-II represents a ligand. Examples of the ligand include ligands disclosed in H. Yersin, *Photochemistry and Photophysics of Coordination Compounds* (Springer-Verlag, 1987) and in Akio Yamamoto, *Yûki Kinzoku Kagaku, Kiso to Ôyô* ("Organic Metal Chemistry, Fundamentals and Applications", Shôkabô, 1982). As the ligand, a halogen ligand (preferably a chlorine ligand), a nitrogen-containing heterocyclic ligand (such as phenylpyridine, benzoquinoline, quinolinole, bipyridyl and phenanthroline), a diketone ligand, and a carboxylic acid ligand are preferred. A nitrogen-containing heterocyclic ligand and a diketone ligand are more preferred.

$n^{21}$ in the general formula K-II represents an integer of 1 to 3, and more preferably 2 or 3. $n^{22}$ in the general formula K-II represents an integer of 0 to 4, and more preferably 0 or 1.

Next, the general formula K-III will be described. $R^{31}$ and $R^{32}$ in the general formula K-III each independently represents a hydrogen atom or a substituent. The substituent may be any group of $R^{11}$ in the general formula K-I. $R^{31}$ in the general formula K-III is preferably a hydrogen atom, an alkyl group, an aryl group, or a heteroaryl group, and more preferably a hydrogen atom. $R^{32}$ in the general formula K-III is preferably a hydrogen atom, an alkyl group, an aryl group, a heteroaryl group, or a fluorine atom, more preferably a hydrogen atom or a fluorine atom, and further preferably a hydrogen atom.

$R^{33}$ to $R^{36}$ in the general formula K-III each independently represents a hydrogen atom or a substituent. Two or more of substituents may be combined with each other to form a cyclic structure. The substituent may be any group of $R^{11}$ in the general formula K-I. $R^{34}$ in the general formula K-III is preferably a hydrogen atom, an alkyl group, a substituted or unsubstituted amino group or an alkoxy group, more preferably a hydrogen atom, an alkyl group, or an alkoxy group, and further preferably a hydrogen atom. $R^{33}$, $R^{35}$, and $R^{36}$ in the general formula K-III are each preferably a hydrogen atom or an alkyl group, and more preferably a hydrogen atom.

Next, the general formula K-IV will be described.

In the general formula K-IV, $R^{41}$, $R^{42}$, $R^{43}$, $R^{44}$, $R^{45}$, and $R^{46}$ each has the same meaning as $R^{31}$, $R^{32}$, $R^{33}$, $R^{34}$, $R^{35}$, and $R^{36}$ in the general formula K-III, and preferred ranges thereof are also the same. $L^{41}$ in the general formula K-IV has the same meaning as $L^{21}$ in the general formula K-II, and a preferred range thereof is also the same. $n^{41}$ in the general formula K-IV represents an integer of 1 to 3, and preferably 1 or 2. $n^{42}$ in the general formula K-IV represents an integer of 0 to 4, and preferably 0 or 1.

Next, the general formula K-V will be described. In the general formula K-V, $R^{53}$, $R^{54}$, $R^{55}$, $R^{56}$, $L^{51}$, $n^{51}$, and $n^{52}$ each has the same meaning as $R^{23}$, $R^{24}$, $R^{25}$, $R^{26}$, $L^{21}$, $n^{21}$, and $n^{22}$ in the general formula K-II, and preferred ranges thereof are also the same.

Next, the general formula K-VI will be described. In the general formula K-VI, $R^{63}$, $R^{64}$, $R^{65}$, $R^{66}$, $L^{61}$, $n^{61}$, and $n^{62}$ each has the same meaning as $R^{43}$, $R^{44}$, $R^{45}$, $R^{46}$, $L^{41}$, $n^{41}$, and $n^{42}$ in the general formula K-IV, and preferred ranges thereof are also the same.

The iridium compound may be either a so-called low molecular weight compound or a so-called oligomer compound and a so-called polymer compound containing repeating units having the partial structure represented by the general formula K-0 (which preferably contain a weight average molecular weight (polystyrene standard) of from 1,000 to 5,000,000, more preferably from 2,000 to 1,000,000, and further preferably from 3,000 to 100,000). Among these, it is preferable that the iridium compound is a low molecular weight compound.

Example compounds (K-1) to (K-25) of the iridium compound having the partial structure represented by the general formula K-0 will be described below, but the invention is not limited to the same.

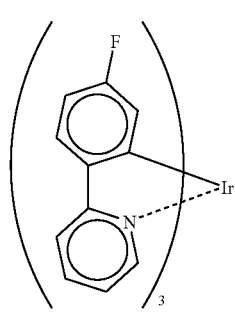

(K-1)

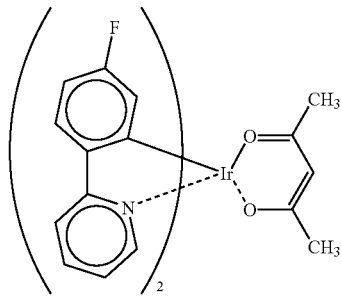

(K-2)

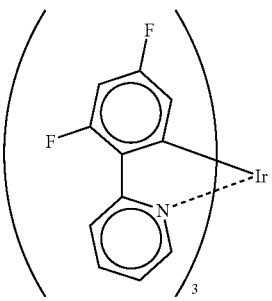

(K-3)

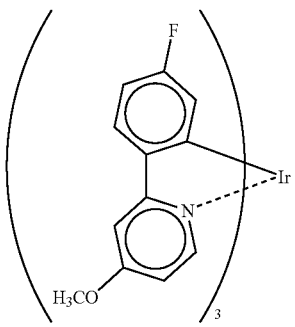

(K-4)

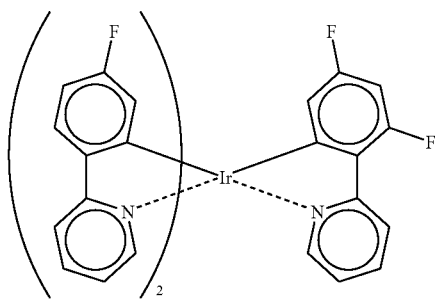

(K-5)

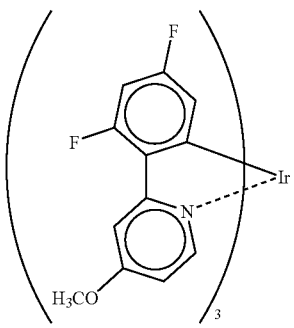

(K-6)

-continued
(K-7)
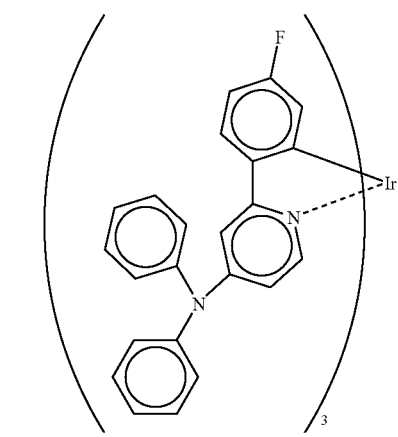
(K-8)
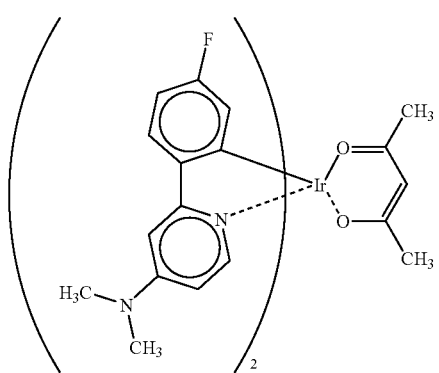
(K-9)
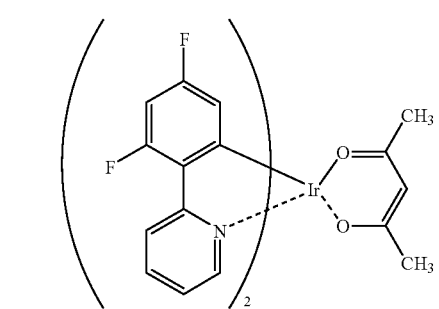
(K-10)
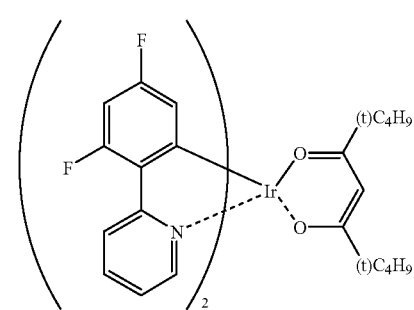
-continued
(K-11)
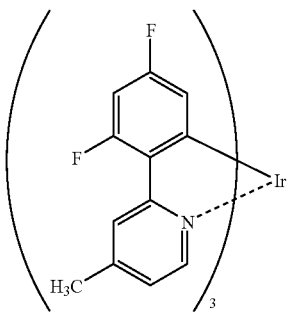
(K-12)
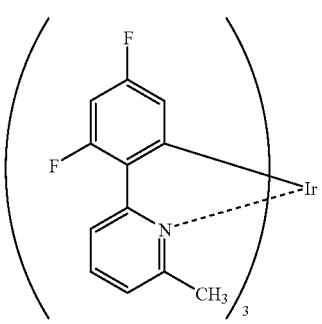
(K-13)
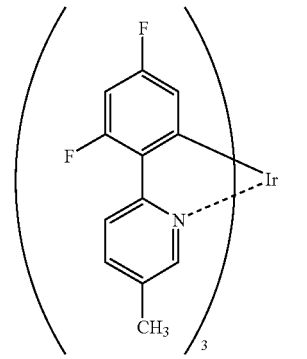
(K-14)
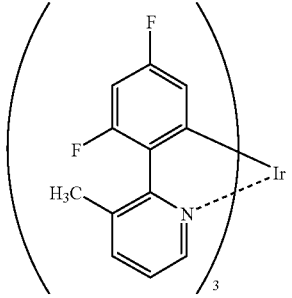
(K-15)
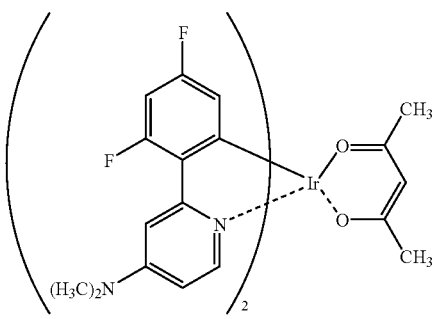

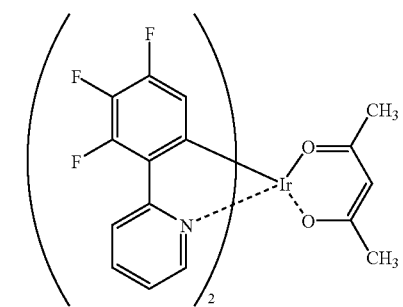
(K-16)
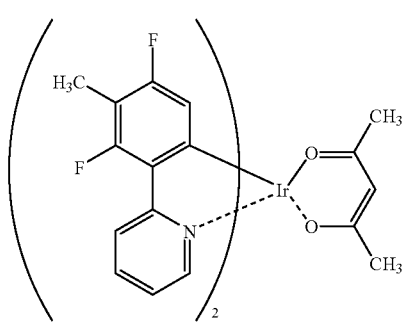
(K-17)
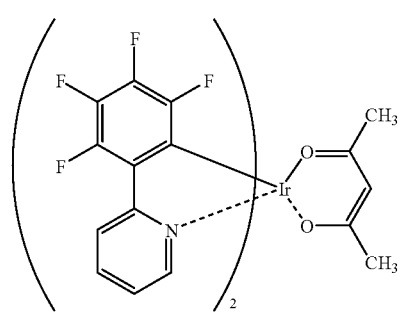
(K-18)
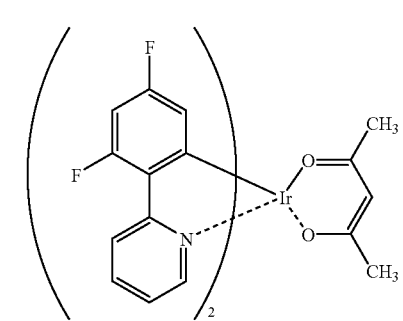
(K-19)
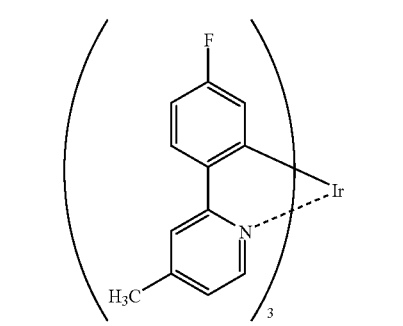
(K-20)
(K-21)
(K-22)
(K-23)
(K-24)

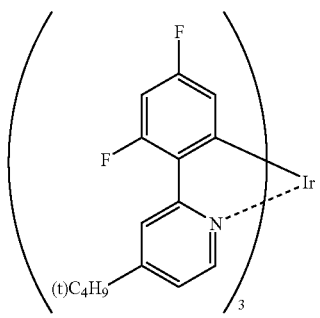

(K-25)

The compound having the partial structure represented by the general formula K-0 can be synthesized by various methods. For example, the various ligands or a dissociated product thereof and the iridium compound are reacted in the presence of a solvent (such as a halogen-substituted hydrocarbon, an alcohol, an ether and water) or the absence of a solvent, and in the presence of a base (such as various kinds of inorganic and organic bases, e.g., sodium methoxide, t-butoxy potassium, triethylamine and potassium carbonate) or the absence of a base, at room temperature or under heating (in which a method of heating by microwave is also effective as well as ordinary heating). Examples of the starting material include iridium (III) chloride, trisacetylacetonato iridium (III), potassium hexachloroiridate (III), potassium hexachloroiridate (IV) and an analogue thereof.

The iridium complex represented by the general formula K-II and the iridium complex represented by the general formula K-IV can be utilized as a material for a light-emitting element and can also be used for medical uses, fluorescent whitening agents, photographic materials, UV absorbing materials, laser dyes, dyes for color filters and color conversion filters.

In another embodiment of the light-emitting element of the present invention, the light-emitting element comprises a light-emitting layer, or a plurality of organic compound layers including the light-emitting layer disposed between a pair of electrodes comprising an anode and a cathode, with at least one layer of the organic compound layers including at least one kind of the iridium compound. Since the iridium compound has the characteristic of emitting blue light at high efficiency, the light emission efficiency of the light-emitting element can be improved by containing the compound in the light-emitting layer. Moreover, since the iridium compound has excellent charge transporting capability, the light emission efficiency of the light-emitting element can also be improved by containing the compound in the charge transporting layer. As a result, a light-emitting element can be provided that reduces energy consumption at the time of light emission and that can emit blue light at a high luminance for a long period of time.

The light-emitting element may further comprise, in addition to the light-emitting layer between the electrodes, a hole implantation layer, a hole transporting layer, an electron implantation layer, an electron transporting layer and a protective layer. These layers may each have other functions. In the light-emitting element, it is preferable to dispose between the cathode and the light-emitting layer a layer containing a compound having an ionization potential of 5.9 eV or more, and more preferably from 6.0 to 7.0 eV. It is more preferable to dispose an electron transporting layer having an ionization potential of 5.9 eV or more. Various kinds of materials can be used to form the layers. In the light-emitting element, the iridium compound may be contained, as the light-emitting material, in the light-emitting layer and also in the charge transporting layer.

The method for forming the layer containing the iridium compound is not particularly limited, and various methods, such as a vacuum deposition method, an LB method, a resistance heating vapor deposition method, an electron beam method, a sputtering method, a molecular accumulation method, a coating method (such as a spin coating method, a casting method and a dip coating method), an ink jet method and a printing method, can be utilized. A resistance heating vapor deposition method and a coating method are preferred from the standpoint of characteristics and production. In particular, the coating method is advantageous in that production cost can be reduced when the light-emitting element is applied to a technology that requires a large area, such as a display.

The layer can be formed by the coating method in the following manner. The iridium compound is dissolved in a solvent to prepare a coating composition, which is then coated on a desired layer (or electrode), followed by drying. The coating composition may contain a resin, and the resin may be in a dissolved state in the solvent or in a dispersed state therein. Examples of the resin include a non-conjugated system polymer (such as polyvinyl carbazole) and a conjugated system polymer (such as a polyolefin series polymer). Specific examples thereof include polyvinyl chloride, polycarbonate, polystyrene, polymetyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethylcellulose, vinyl acetate, ABS resin, polyurethane, melamine resin, unsaturated polyester resin, alkyd resin, epoxy resin and silicone resin.

The anode is to supply holes to the hole implantation layer, the hole transporting layer and the light-emitting layer, and may comprise a metal, an alloy, a metallic oxide, an electroconductive compound or a mixture thereof, and preferably a material having a work function of 4 eV or more. Specific examples thereof include electroconductive metallic oxides, such as tin oxide, zinc oxide, indium oxide and indium tin oxide (ITO), metals, such as gold, silver, chromium and nickel, mixtures or accumulated products of metal and electroconductive metallic oxide, inorganic electroconductive substances, such as copper iodide and copper sulfide, organic electroconductive materials, such as polyaniline, polythiophen and polypyrrole, and accumulated products of these and ITO. Among these, electroconductive metallic oxide is preferable, and ITO is particularly preferable from the standpoint of productivity, high electroconductivity and transparency. The film thickness of the anode can be appropriately selected depending on the material, and is preferably from 10 nm to 5 µm, more preferably from 50 nm to 1 µm, and further preferably from 100 to 500 nm.

The anode is generally formed as a layer on a transparent substrate, such as soda lime glass, non-alkali glass or a transparent resin substrate. When glass is used as the transparent substrate, the glass material is preferably non-alkali glass in order to reduce eluting ions from the glass. When soda lime glass is used, it is preferable to use a soda lime glass having a barrier coating of, for example, silica. The thickness of the substrate is not particularly limited as long as it sufficiently maintains mechanical strength, and is generally 0.2 mm or more, and preferably 0.7 mm or more when glass is used.

The anode can be produced by various methods depending on the material, and in the case of ITO, the film thereof may be produced by an electron beam method, a sputtering method, a resistance heating vapor deposition method, a chemical reaction method (a sol-gel method) and coating of an indium tin oxide dispersion. When the anode is subjected to various treatments, such as cleaning, the driving voltage of the light-emitting element can be decreased, and light emission efficiency thereof can be improved. In the case of ITO, for example, a UV-ozone treatment and a plasma treatment are effective.

The cathode is to supply electrons to the electron implantation layer, the electron transporting layer and the light-emitting layer, and is selected in consideration of adhesion to the layer adjacent to the cathode, such as the electron implantation layer, the electron transporting layer and the light-emitting layer, ionization potential and stability. Examples of the material of the cathode include metals, alloys, metallic halogenides, metallic oxides, electroconductive compounds and mixtures thereof. Specific examples thereof include alkali metals (such as Li, Na and K) and fluorides or oxides thereof, alkaline earth metals (such as Mg and Ca) and fluorides or oxides thereof, gold, silver, lead, alloys or metallic mixtures of sodium and potassium, alloys or metallic mixtures of lithium and aluminum, alloys or metallic mixtures of magnesium and silver, and rare earth metals, such as indium and ytterbium. Among these, a material having a work function of 4 eV or less is preferable, and aluminum, an alloy or a metallic mixture of lithium and aluminum and an alloy of a metallic mixture of magnesium and silver are more preferable. The cathode may have a single layer structure of the compounds and the mixture, or an accumulated layer structure containing the compounds and the mixtures. For example, accumulated layer structures of aluminum/lithium fluoride and aluminum/lithium oxide are preferable. The film thickness of the cathode can be appropriately selected depending on the material, and is preferably from 10 nm to 5 µm, more preferably from 50 nm to 1 µm, and further preferably from 100 nm to 1 µm.

The cathode can be produced by various methods, such as an electron beam method, a sputtering method, a resistance heating vapor deposition method and a coating method, and a single component of a metal may be vapor-deposited or, alternatively, two or more components may be simultaneously vapor-deposited. Furthermore, plural metals may be simultaneously vapor-deposited to form an alloy electrode, and an alloy having been prepared may be vapor-deposited.

The sheet resistance of the anode and the cathode is preferably as low as possible, and is preferably several hundreds Ω per square or less.

The material of the light-emitting layer is not particularly limited as long as it is capable of forming a layer in which it is possible for holes to be implanted thereto from the anode, the hole implantation layer or the hole transporting layer upon application of an electric field, and in which it is possible for electrons to be implanted thereto from the cathode, an electron implantation layer or the electron transporting layer. The material of the light-emitting layer must also function to move the implanted charge and to provide a place for the recombination of holes and electrons to emit light. The light-emitting layer preferably contains the iridium compound as the light-emitting material since it enables blue light emission with high efficiency. However, when the iridium compound is contained in the organic compound layers other than the light-emitting layer, other light-emitting materials may be used. Examples of other light-emitting materials include various kinds of metallic complexes and rare earth complexes of a benzoxazole derivative, a benzimidazole derivative, a benzthiazole derivative, a styrylbenzene derivative, a polyphenyl derivative, a diphenylbutadiene derivative, a tetraphenylbutadiene derivative, a naphthalimide derivative, a coumarin derivative, a perylene derivative, a perynone derivative, an oxadiazole derivative, an aldadine derivative, a pyraridine derivative, a cyclopentadiene derivative, a bisstyrylanthracene derivative, a quinacridone derivative, a pyrrolopyridine derivative, a thiadiazolopyridine derivative, a cyclopentadiene derivative, a styrylamine derivative, an aromatic dimethylidyne derivative, and an 8-quinolinole derivative, a polymer compound, such as polythiophene, polyphenylene and polyphenylenevinylene, and an organic silane compound. In the light-emitting layer, any of the other light-emitting compounds may be used in combination with the iridium compound.

A host material with the iridium compound as a guest material may be contained in the light-emitting layer along with the iridium compound. Examples of the host material include one having a carbazole skeleton, one having a diarylamine skeleton, one having a pyridine skeleton, one having a pyrazine skeleton, one having a triazine skeleton and one having an arylsilane skeleton. The host material preferably has the energy level of the minimum triplet excited state, $T_1$, which is greater than the level of $T_1$ of the guest material. The host material may be either a low molecular weight compound or a high molecular weight compound. The host material and the light-emitting material, such as the iridium compound, are subjected to simultaneous vapor deposition to form the light-emitting layer comprising the host material doped with the light-emitting material.

The film thickness of the light-emitting layer is not particularly limited, and in general, it is preferably from 1 nm to 5 µm, more preferably from 5 nm to 1 µm, and further preferably from 10 nm to 500 nm.

The method for forming the light-emitting layer is not particularly limited, and a resistance heating vapor deposition method, an electron beam method, a sputtering method, a molecular accumulation method, a coating method (such as a spin coating method, a casting method and a dip coating method), an inkjet method, a printing method and an LB method may be used with a resistance heating vapor deposition method and the coating method being preferred.

The material for the hole implantation layer and the hole transporting layer may be a material having one of a function to implant holes from the anode, a function to transport the holes, and a function to obstruct electrons implanted from the cathode. Specific examples thereof include a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidyne series compound, a porphyrin series compound, an oligomer of an electroconductive polymer, such as a polysilane series compound, a poly(N-vinylcarbazole) derivative, an aniline series copolymer, a thiophene oligomer and polythiophene, an organic silane derivative, and the above-described iridium compound. The film thickness of the hole implantation layer and the hole transporting layer is not particularly limited, and in general, it is preferably from 1 nm to 5 μm, more preferably from 5 nm to 1 μm, and further preferably from 10 to 500 nm. The hole implantation layer and the hole transporting layer may have a single layer structure of one kind or two or more kinds of materials or, alternatively, a multilayer structure comprising plural layers having the same composition or different compositions. The same forming methods as those listed for the formation of the layer containing the iridium compound can be applied to the formation of the hole implantation layer and the hole transporting layer.

The material for the electron implantation layer and the electron transporting layer may be a material having one of a function to implant electrons from the cathode, a function to transport the electrons, and a function to obstruct holes implanted from the anode. Specific examples thereof include a triazole derivative, an oxazole derivative, an oxadiazole derivative, an imidazole derivative, a fluorenone derivative, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic acid anhydride of an aromatic ring, such as naphthalene and perylene, a phthalocyanine derivative, and various metallic complexes, such as a metallic complex of an 8-quinolinol derivative and a metallic complex having metal phthalocyanine, benzoxazole or benzotiazole as a ligand, an organic silane derivative, and the iridium compound. The film thickness of the electron implantation layer and the electron transporting layer is not particularly limited, and in general, it is preferably from 1 nm to 5 μm, more preferably from 5 nm to 1 μm, and further preferably from 10 to 500 nm. The electron implantation layer and the electron transporting layer may have a single layer structure of one kind or two or more kinds of the materials or, alternatively, a multilayer structure comprising plural layers having the same composition or different compositions. The same forming methods as those listed for forming the layer containing the iridium compound can be applied to the formation of the electron implantation layer and the electron transporting layer.

The material for the protective layer may be those having a function to suppress entrance of substances that accelerate deterioration of the element, such as moisture and oxygen, into the element. Specific examples thereof include metals, such as In, Sn, Pb, Au, Cu, Ag, Al, Ti and Ni, metallic oxides, such as MgO, SiO, SO$_2$, Al$_2$O$_3$, GeO, NiO, CaO, BaO, Fe$_2$O$_3$, Y$_2$O$_3$ and TiO$_2$, metallic nitrides, such as SiN$_x$ and SiN$_x$O$_y$, metallic fluorides, such as MgF$_2$, LiF, AlF$_3$ and CaF$_2$, polyethylene, polypropylene, polymethyl methacrylate, polyimide, polyurea, polytetrafluoroethylene, polychlorotrifluoroethylene, polydichlorodifluoroethylene, a copolymer of chlorotrifluoroethylene and dichlorodifluoroethylene, a copolymer obtained by copolymerizing a monomer mixture containing tetrafluoroethylene and at least one kind of a comonomer, a fluorine-containing copolymer having a cyclic structure in a copolymer main chain, a water absorbing substance having a water absorption of 1% or more, and a moisture preventing substance having a water absorption of 0.1% or less. The method for forming the protective layer is also not particularly limited, and those listed for methods of producing the layer containing the iridium compound can be utilized.

The light-emitting element of the present invention can be applied to technologies in various fields, such as display devices, displays, backlights, electrophotography, illumination light sources, recording light sources, exposure light sources, read light sources, signs, signboards and interior, optical communication.

The present invention will be further described in detail with reference to the following examples, but the present invention should not be construed as being limited to the same.

SYNTHESIS EXAMPLE 1

Synthesis of Example Compound K-1

1.77 g of 2-(4-fluorophenyl)pyridine, 0.5 g of trisacetylacetonato iridium (III) and 30 ml of glycerol were mixed and then stirred under a nitrogen stream at 200° C. for 4 hours. After cooling to room temperature, 200 ml of methanol was added thereto, and a solid matter thus deposited was filtered out. The solid matter was purified with silica gel column chromatography (eluent: chloroform) to obtain 0.5 g of a pale yellow solid matter. The NMR measurement thereof revealed that the resulting compound was the example compound K-1.

The phosphorescence quantum yield of the resulting example compound K-1 was measured after degassing oxygen (solvent: toluene, concentration: $5.0 \times 10^{-6}$ mol/L), and it was 90%. The phosphorescence emission maximum wavelength λmax was 477 nm.

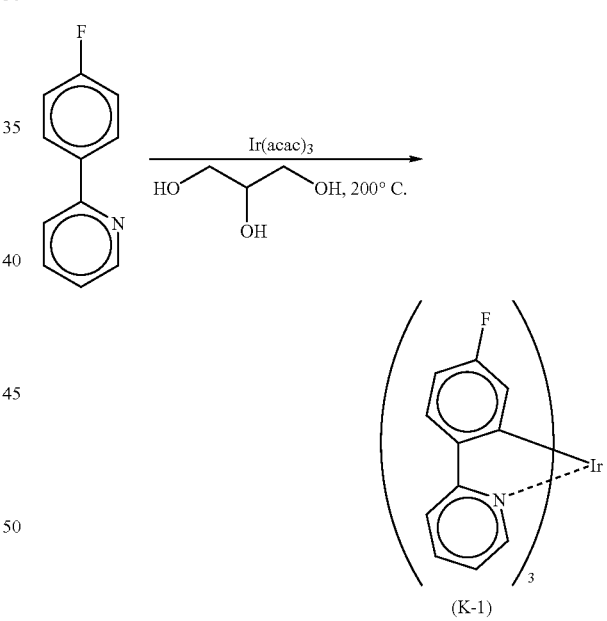

(K-1)

SYNTHESIS EXAMPLE 2

Synthesis of Example Compound K-3

3.0 g of 2-(2,4-difluorophenyl)pyridine, 1.3 g of trisacetylacetonato iridium (III) and 50 ml of glycerol were mixed and then stirred under a nitrogen stream at 200° C. for 4 hours. After cooling to room temperature, 200 ml of methanol was added thereto, and a solid matter thus deposited was filtered out. The solid matter was purified with silica gel column chromatography (eluent: chloroform) to obtain 0.8 g of a pale yellow solid matter. The NMR measurement thereof revealed that the resulting compound was the example compound K-3.

The phosphorescence quantum yield of the resulting example compound K-3 was measured after degassing oxygen (solvent: toluene, concentration: $5.0 \times 10^{-6}$ mol/L), and it was 70%. The phosphorescence emission maximum wavelength λmax was 470 nm.

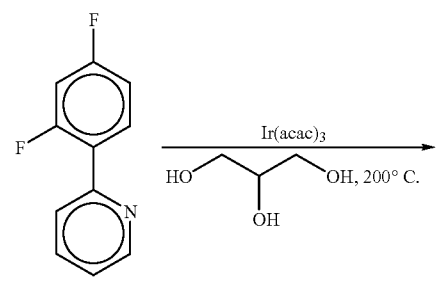

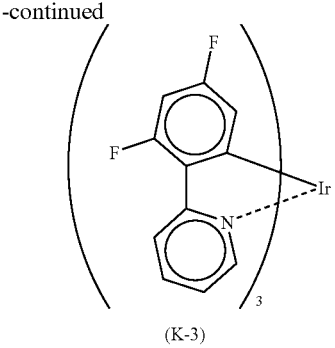

(K-3)

SYNTHESIS EXAMPLE 3

Synthesis of Example Compound K-9

10 ml of chloroform was added to 0.2 g of compound (a) and 0.07 ml of acetylacetone, and 0.13 ml of methanol solution of sodium methoxide (28% by weight) was further added thereto and then stirred under a reflux for 6 hours. After cooling to room temperature, 50 ml of chloroform and 50 ml of water were added thereto, and an organic layer was separated. The organic layer was purified with silica gel column chromatography (eluent: chloroform) to obtain 0.1 g of a pale yellow solid matter. The NMR measurement thereof revealed that the resulting compound was the example compound K-9.

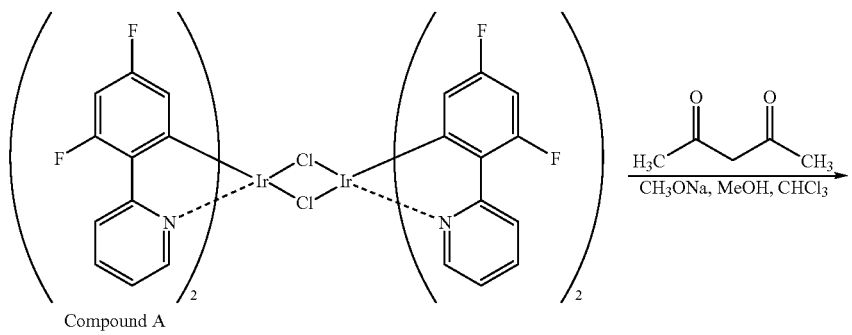

Compound A

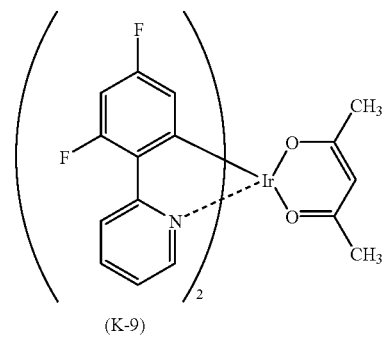

(K-9)

SYNTHESIS EXAMPLE 4

Synthesis of Example Compound K-11

1.0 g of 2-(2,4-difluorophenyl)-4-methylpyridine, 1.0 g of trisacetylacetonato iridium (III) and 30 ml of glycerol were mixed and then stirred under a nitrogen stream at 200° C. for 4 hours. After cooling to room temperature, 200 ml of water was added thereto, and a solid matter thus deposited was filtered out. The solid matter was purified with silica gel column chromatography (eluent: chloroform) to obtain 0.2 g of a pale yellow solid matter. The NMR measurement thereof revealed that the resulting compound was the example compound K-11.

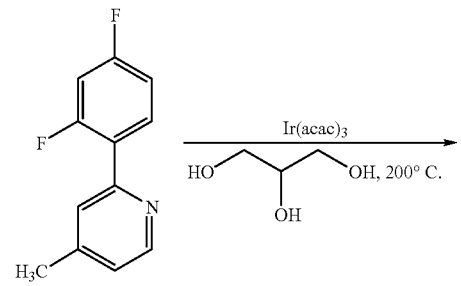

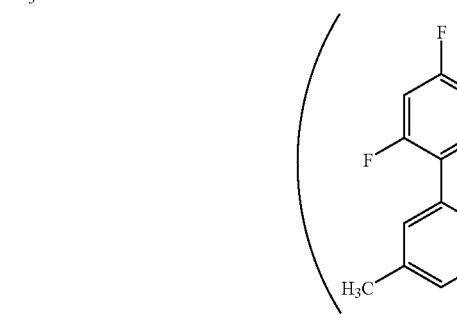

(K-11)

COMPARATIVE EXAMPLE 1

A cleaned ITO substrate was installed in a vapor deposition apparatus, on which α-NPD (N,N'-diphenyl-N,N'-di(α-naphthyl)benzidine was vapor-deposited to a thickness of 40 nm, the compound A and the compound B (disclosed in *Applied Physics Letters*, Vol. 75, No. 1 (5 Jul. 1999)) shown below were vapor-deposited (weight ratio: 10/1) to a thickness of 24 nm, and the compound E shown below was further vapor-deposited thereon to a thickness of 24 nm, so as to form an organic thin film. After providing a patterned mask (providing a light emission area of 4 mm×5 mm) on the organic thin film, magnesium and silver (10/1) were simultaneously vapor-deposited to a thickness of 50 nm, and then silver was vapor-deposited to a thickness of 50 nm, whereby an organic EL device was produced.

The phosphorescence quantum yield of the compound B was measured in the same manner as the example compound K-1, and it was 70%. The phosphorescence emission maximum wavelength λmax was 507 mm.

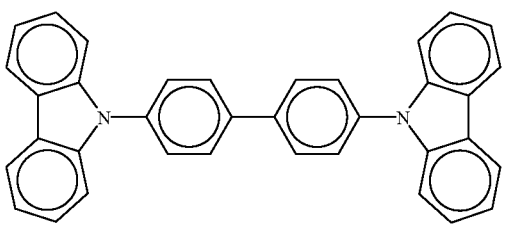

Compound A

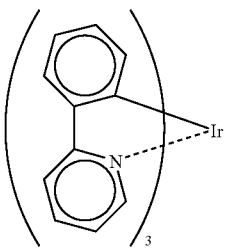

Compound B (described in Applied Physics Letters, Vol. 75, No. 1 (July 5, 1999))

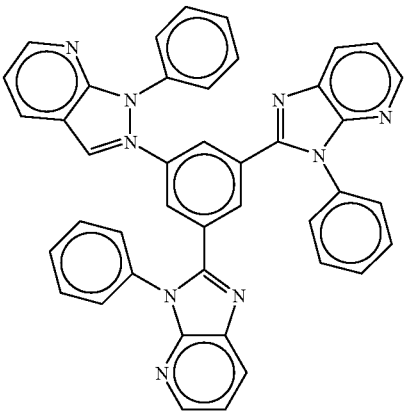

Compound E

The resulting organic EL device was subjected to light emission by applying a constant direct current voltage by using a source measuring unit, Type 2400 produced by Toyo Corp., and the brightness and the light emission wavelength were measured by using a luminance meter, BM-8 produced by Topcon Corp., and a spectrum analyzer, PMA-11 produced by Hamamatsu Photonics Co., Ltd., respectively. As a result, green light emission of a light emission wavelength λmax of 516 nm and a CIE chromaticity value (x, y) of (0.29, 0.62) was obtained, and the external quantum efficiency thereof was 13.6%.

COMPARATIVE EXAMPLE 2

An organic EL device was produced in the same manner as in Comparative Example 1 except that the compound C (disclosed in *Polymer Preprints*, Vol. 41(1), p. 770 (2000)) shown below was used instead of the compound B and then evaluated in the same manner. As a result, green light emission of a light emission wavelength λmax of 505 nm and a CIE chromaticity value (x, y) of (0.27, 0.57) was obtained, and the external quantum efficiency thereof was 3.3%.

Compound C (described in *Polymer Preprints*, Vol. 41(1), p. 770 (2000))

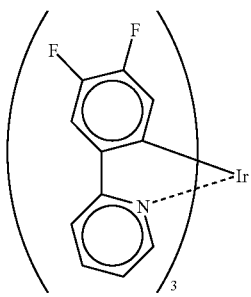

It was understood from the results of Comparative Examples 1 and 2 that only green light emission could be obtained by the organic EL devices containing the known orthometalated iridium complexes.

COMPARATIVE EXAMPLE 3

A cleaned ITO substrate was installed in a vapor deposition apparatus, on which α-NPD (N,N'-diphenyl-N,N'-di(α-naphthyl)benzidine) was vapor-deposited to a thickness of 40 nm, and the following compound F (DPVBi) was vapor-deposited thereon to a thickness of 20 nm. The compound E was further vapor-deposited thereon to a thickness of 40 nm, and the cathode was vapor-deposited in the same manner as in Comparative Example 1, so as to produce an organic EL device.

The resulting organic EL device was subjected to light emission by applying a constant direct current voltage in the same manner as in Comparative Example 1. As a result, blue light emission of a CIE chromaticity value (x, y) of (0.15, 0.20) was obtained, but the external quantum efficiency thereof was as low as 1.2%. It was understood from the results of Comparative Example 3 that the known blue light-emitting element had a low external quantum efficiency, which was far lower than 5%.

Compound F (DPVBi)

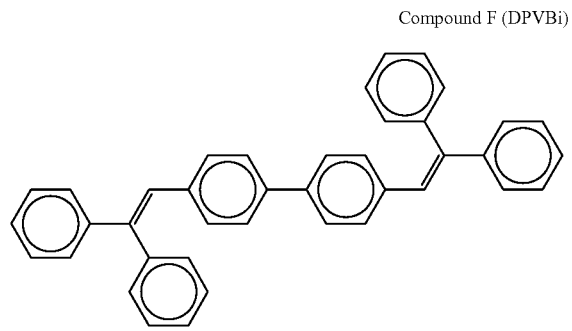

EXAMPLE 1

An organic EL device was produced in the same manner as in Comparative Example 1 except that the example compound K-I was used instead of the compound B and then evaluated in the same manner. As a result, blue light emission of a light emission wavelength λmax of 486 nm and a CIE chromaticity value (x, y) of (0. 18, 0.49) was obtained, and the external quantum efficiency thereof was 5.8%.

EXAMPLE 2

An organic EL device was produced in the same manner as in Comparative Example 1 except that the example compound K-1 was used instead of the compound B, the compound D shown below was used instead of the compound A, and then evaluated in the same manner. As a result, blue light emission of a light emission wavelength λmax of 487 nm and a CIE chromaticity value (x, y) of (0.22, 0.53) was obtained, and the external quantum efficiency thereof was 10.5%.

Compound D

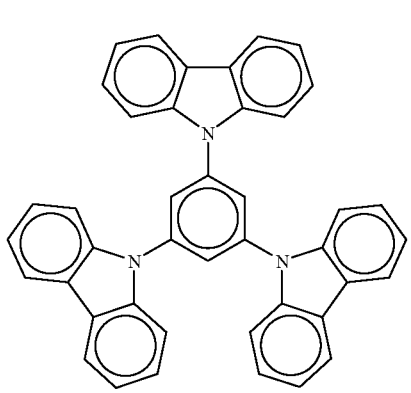

EXAMPLE 3

A cleaned ITO substrate was installed in a vapor deposition apparatus, on which TPD (N,N'-diphenyl-N,N'-di(m-tolyl)benzidine was vapor-deposited to a thickness of 50 nm, the compound K-1 and the compound D were vapor-deposited (weight ratio: 1/17) to a thickness of 36 nm, and the compound G was further vapor-deposited thereon to a thickness of 36 nm, so as to form an organic thin film. After providing a patterned mask (providing a light emission area of 4 mm×5 mm) on the organic thin film, lithium fluoride was vapor-deposited in the vapor deposition apparatus to a thickness of 3 nm, and then aluminum was vapor-deposited to a thickness of 40 nm, whereby an organic EL device was produced. As a result, blue light emission of a light emission maximum wavelength λmax of 485 nm and a CIE chromaticity value (x, y) of (0.19, 0.51) was obtained, and the external quantum efficiency thereof was 19.1%.

Compound G

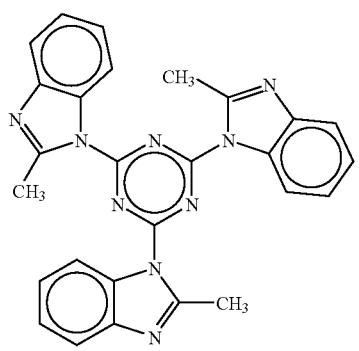

EXAMPLE 4

An organic EL device was produced in the same manner as in Example 3 except that the example compound K-3 was used instead of the example compound K-1 and then evaluated in the same manner. As a result, blue light emission of a light emission maximum wavelength λmax of 473 nm and a CIE chromaticity value (x, y) of (0.15, 0.37) was obtained, and the external quantum efficiency thereof was 12.9%.

EXAMPLE 5

An organic EL device was produced in the same manner as in Example 3 except that the example compound K-9 was used instead of the example compound K-1 and then evaluated in the same manner. As a result, blue light emission of a light emission maximum wavelength λmax of 480 nm and a CIE chromaticity value (x, y) of (0.20, 0.52) was obtained, and the external quantum efficiency thereof was 11.4%.

A blue light-emitting EL element of high efficiency can be produced by producing and evaluating EL elements containing the compounds of the present invention in the similar manner. Blue light-emitting elements of a coating type containing a non-conjugated system polymer (such as polyvinyl carbazole) and a conjugated system polymer (such as a polyolefin series polymer) can also be produced.

As described in the foregoing, the light-emitting element according to the present invention can emit blue light at high efficiency in comparison to conventional blue light-emitting elements. When the light-emitting element of the present invention is used as a display element, electric power consumption can be greatly reduced, and a large area display and long term use can be realized. A white light-emitting element of high efficiency can be produced by a combination of a light-emitting material of red to orange colors and a light-emitting element of red to orange colors on the basis of the blue light-emitting element of the present invention. Furthermore, according to the present invention, an iridium complex that emits blue light at high efficiency can be provided.

What is claimed is:

1. A light-emitting element comprising a pair of electrodes and a light-emitting layer, or a plurality of organic compound layers containing a light-emitting layer between the pair of electrodes, wherein the light-emitting layer, or the plurality of organic compound layers containing a light-emitting layer, comprises at least one kind of compound having a partial structure represented by the following general formula K-III:

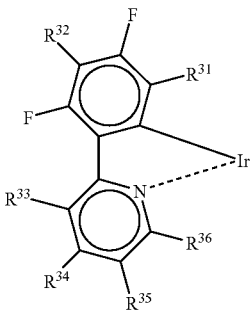

General formula K-III wherein $R^{31}$ and $R^{33}$ to $R^{36}$ each independently represents hydrogen or a substituent; $R^{32}$ represents hydrogen; and two or more of $R^{33}$ to $R^{36}$ may be combined with one another to form a cyclic structure;

wherein the light-emitting element has a light emission maximum wavelength of 420-480 nm;

wherein the at least one kind of compound having the partial structure represented by general formula K-III is of the following general formula K-IV:

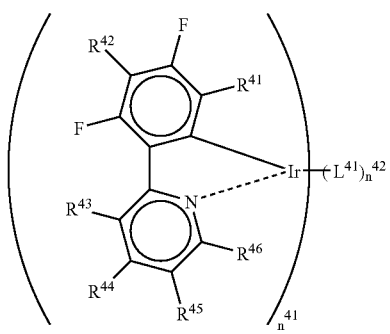

General formula K-IV wherein $R^{41}$ and $R^{43}$ to $R^{46}$ each independently represents hydrogen or a substituent; $R^{42}$ represents hydrogen; $L^{41}$ represents a ligand; $n^{41}$ represents an integer of 1 to 3; and $n^{42}$ represents an integer of 0 to 4;

wherein the light-emitting layer comprises at least one host material having a unit which is selected from the group consisting of a pyridine unit, a pyrazine unit, a triazine unit, and an arylsilane unit.

2. The light-emitting element of claim 1, wherein $R^{41}$ is hydrogen, an alkyl group, an aryl group, or a heteroaryl group.

3. The light-emitting element of claim 1, wherein $R^{44}$ is hydrogen, an alkyl group, a substituted or unsubstituted amino group, or an alkoxy group.

4. The light-emitting element of claim 1, wherein $R^{43}$, $R^{45}$ and $R^{46}$ each independently represents hydrogen or an alkyl group.

5. The light-emitting element of claim 1, wherein $n^{41}$ is 3 and $n^{42}$ is 0.

6. The light-emitting element of claim 1, wherein $L^{41}$ is at least one ligand selected from the group consisting of a halogen ligand, a nitrogen-containing heterocyclic ligand, a diketone ligand and a carboxylic acid ligand.

7. The light-emitting element of claim 1, further comprising at least one layer which is selected from the group consisting of a hole implantation layer, a hole-transporting layer, an electron-implantation layer, an electron-transporting layer and a protective layer.

8. The light-emittingelement of claim 1, wherein the y value of the CIE chromaticity of light emission of the light-emitting element is 0.40 or less.

9. A light-emitting element comprising a pair of electrodes and a light-emitting layer, or a plurality of organic compound layers containing a light-emitting layer between the pair of electrodes, wherein the light-emitting layer, or the plurality of organic compound layers containing a light-emitting layer, comprises at least one kind of compound having a partial structure represented by the following general formula K-III:

General Formula K-III

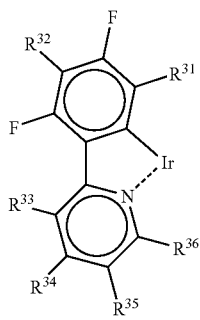

General Formula K-III wherein $R^{31}$ and $R^{33}$ to $R^{36}$ each independently represents hydrogen or a substituent; $R^{32}$ represents hydrogen; and two or more of $R^{33}$ to $R^{36}$ may be combined with one another to form a cyclic structure;

wherein the y value of the CIE chromaticity of light emission of the light-emitting element is 0.40 or less;

wherein the at least one kind of compound having the partial structure represented by general formula K-III is of the following general formula K-IV:

General Formula K-IV

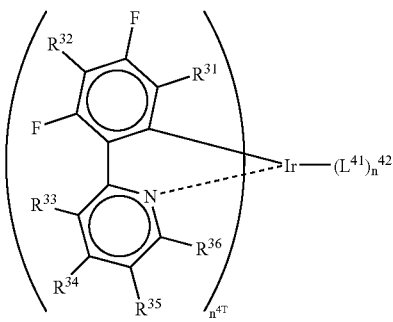

wherein $R^{41}$ and $R^{43}$ to $R^{46}$ each independently represents hydrogen or a substituent: $R^{42}$ represents hydrogen; $L^{41}$ represents a ligand; $n^{41}$ represents an integer of 1 to 3; and $n^{42}$ represents an integer of 0 to 4;

wherein the light-emitting layer comprises at least one host material having a unit which is selected from the group consisting of a pyridine unit, a pyrazine unit, a triazine unit, and an arylsilane unit.

10. The light-emitting element of claim 9, wherein $R^{41}$ is hydrogen, an alkyl group, an aryl group, or a heteroaryl group.

11. The light-emitting element of claim 9, wherein $R^{44}$ is hydrogen, an alkyl group, a substituted or unsubstituted amino group, or an alkoxy group.

12. The light-emitting element of claim 9, wherein $R^{43}$, $R^{45}$ and $R^{46}$ each independently represents hydrogen or an alkyl group.

13. The light-emitting element of claim 9, wherein $n^{41}$ is 3 and $n^{42}$ is 0.

14. The light-emitting element of claim 9, wherein $L^{41}$ is at least one ligand selected from the group consisting of a halogen ligand, a nitrogen-containing heterocyclic ligand, a diketone ligand and a carboxylic acid ligand.

15. The light-emitting element of claim 9, further comprising at least one layer which is selected from the group consisting of a hole-implantation layer, a hole-transporting layer, an electron-implantation layer, an electron-transporting layer and a protective layer.

* * * * *